US008236255B2

(12) United States Patent
Takayama et al.

(10) Patent No.: US 8,236,255 B2
(45) Date of Patent: Aug. 7, 2012

(54) SLIDE TREATMENT APPARATUS AND METHODS FOR USE

(75) Inventors: Glenn K. Takayama, Danville, CA (US); Ken K. Tseung, Fremont, CA (US); Norman K. Rhett, San Ramon, CA (US); Wai Bun Wong, Fremont, CA (US); Samuel Burd, Oakland, CA (US); George A. Harter, Berkeley, CA (US); Douglas C. Morrison, Fremont, CA (US)

(73) Assignee: Lab Vision Corporation, Freemont, CA (US)

( * ) Notice: Subject to any disclaimer, the term of this patent is extended or adjusted under 35 U.S.C. 154(b) by 1321 days.

(21) Appl. No.: 11/002,164

(22) Filed: Dec. 2, 2004

(65) Prior Publication Data

US 2006/0120925 A1    Jun. 8, 2006

(51) Int. Cl.
*B01L 3/00* (2006.01)
(52) U.S. Cl. .............. 422/500; 422/50; 422/63; 422/64; 422/65; 422/67; 422/501; 422/502
(58) Field of Classification Search .............. 422/63–67, 422/99–100, 50, 500–502; 206/474
See application file for complete search history.

(56) References Cited

U.S. PATENT DOCUMENTS

| | | | | |
|---|---|---|---|---|
| 4,609,796 A | * | 9/1986 | Bergsma | 200/84 C |
| 5,049,510 A | | 9/1991 | Repasi et al. | |
| 5,273,905 A | * | 12/1993 | Muller et al. | 435/286.5 |
| 5,453,487 A | * | 9/1995 | Chang et al. | 530/334 |
| 5,601,650 A | * | 2/1997 | Goldbecker et al. | 118/697 |
| 5,958,341 A | | 9/1999 | Chu | |
| 6,074,868 A | | 6/2000 | Blumenfeld | |
| 6,228,634 B1 | | 5/2001 | Blumenfeld et al. | |
| 6,544,798 B1 | | 4/2003 | Christensen et al. | |
| 6,580,056 B1 | | 6/2003 | Tacha | |
| 6,582,962 B1 | | 6/2003 | Richards et al. | |
| 6,586,713 B2 | | 7/2003 | Essenfeld et al. | |

(Continued)

FOREIGN PATENT DOCUMENTS

JP    7333123 A    12/1995

(Continued)

OTHER PUBLICATIONS

USPTO, International Search Report and Written Opinion of the International Searching Authority, International Application No. PCT/US2005/043105, Mailed Oct. 30, 2006 (8 pages).

(Continued)

*Primary Examiner* — Jyoti Nagpaul
(74) *Attorney, Agent, or Firm* — Wood, Herron & Evans, LLP

(57) ABSTRACT

An apparatus for treating slides has a base with a cavity, and a heater is located on a surface of the cavity. A tank, which supports a slide rack with the slides submerged in a slide treatment solution, is placed in the cavity with a tank surface immediately adjacent the heater. A temperature sensor is mounted in the base and is operable to provide a feedback signal representing a temperature of the liquid in the tank. A cover is removably hinged on the base to cover the tank. A control system is connected to the heater and the temperature sensor and has a user input/output that is operable to select a set temperature of the liquid and a cycle time.

8 Claims, 7 Drawing Sheets

U.S. PATENT DOCUMENTS

| | | | |
|---|---|---|---|
| 6,632,598 B1 | 10/2003 | Zhang et al. | |
| 6,756,015 B2 * | 6/2004 | Dalkidis et al. | 422/68.1 |
| 6,793,890 B2 | 9/2004 | Morales et al. | |
| 2001/0043884 A1 | 11/2001 | Essenfeld et al. | |
| 2003/0090364 A1 * | 5/2003 | Cardinale et al. | 340/5.54 |
| 2003/0100043 A1 | 5/2003 | Kalra et al. | |
| 2004/0004075 A1 | 1/2004 | Morales et al. | |
| 2004/0009098 A1 | 1/2004 | Torre-Bueno | |

FOREIGN PATENT DOCUMENTS

| | | |
|---|---|---|
| WO | 2004057307 A1 | 7/2004 |

OTHER PUBLICATIONS

Australian Government, IP Australia, Examiner's Report issued in related Australian patent application No. 2005312026 dated Mar. 3, 2010.

Australian Patent Office, Examiner's First Report on Patent Application No. 2005312026, LabVision Corporation, Mar. 3, 2010, 2 pgs.

Chinese Patent Office, Office Action and English Translation issued in related Chinese application No. 20058004131.7 dated Feb. 13, 2012.

* cited by examiner

SLIDE TREATMENT APPARATUS AND METHODS FOR USE

FIELD OF THE INVENTION

The invention relates generally to a slide treatment apparatus and methods more particularly, to an apparatus for treating slides bearing biological specimens in a heated liquid.

BACKGROUND OF THE INVENTION

A vast majority of specimens for histological studies are fixed, paraffin-embedded tissues. In order for sections taken from paraffin-embedded tissues to be stained or otherwise processed for examination and analysis, the paraffin must be removed from the sections. Early methods for deparaffinization employed flammable, volatile, and toxic organic solvents, such as xylene, to remove the parafin. However, safer, non-organic deparaffinizing agents are now commercially available. Further, U.S. Pat. No. 6,632,598 describes a deparaffinization solvent that is composed of non-polar hydrocarbons with boiling points between 140° C. and 250° C., polar organic solvents and surfactants. Non-flammable, non-volatile solvents are typically used in conjunction with heating to temperatures at or above the melting temperature of paraffin, approximately 50-57° C. For example, deparaffinization of a tissue section may be done by placing the slide with the tissue in an oven with resistance heating elements, a microwave oven, a pressure cooker, steamer, water bath or other thermal platform.

Specimens processed with formalin and/or other fixatives, and intended for certain immunohistochemistry (IHC) procedures, benefit from additional treatment to expose antigenic cites, referred to as antigen (epitope) retrieval, either during or after deparaffinization. Formalin is an effective fixative because it cross-links proteins making the tissue resistant to decomposition. But cross-linking can mask epitopes and prevent recognition of these sites by antibody reagents used in IHC procedures. Thus, the purpose of antigen retrieval processes is to unmask hidden epitopes, usually by way of a semi-destructive method.

Early methods of unmasking antigens make use of proteolytic enzymes to partially digest a tissue section. A major drawback with enzymatic digestion is that specimens tend to vary as to the amount of time needed for sufficient antigen retrieval, yet even a mild overexposure can lead to destruction of tissue morphology or loss of tissue from the slide and generally increases non-specific background interaction with antibody reagents.

Microwave heating has become a popular replacement for, or supplement to, enzymatic digestion to unmask antigens in fixed tissue sections. However, microwave heating is not ideal. Microwave ovens generally are not capable of uniform heat distribution throughout the heating compartment, increasing the risk that some slides may be under-heated while others are overheated. Microwave heating produces vigorous boiling leading to the evaporation of the liquid antigen retrieval reagent in contact with the slides, so typically, the method requires several rounds of microwave exposure interrupted by re-filling the containers holding the slides and treatment solution. Also, because microwave heating is difficult to control, tissue can be damaged and/or lost during processing.

Several automated instruments are commercially available that provide protocols for pre-treatment, including deparaffinization and antigen retrieval, and staining, but while these instruments allow different staining and IHC procedures to be performed simultaneously, they do not permit simultaneous performance of deparaffinization and/or antigen retrieval either together or with any other procedure. An automated antigen retrieval system, the "i1000™", manufactured and sold by BioGenex (San Ramon, Calif.), is an exception, capable of simultaneously performing deparaffinization and antigen retrieval, but it uses microwave heating.

While such slide treatment devices often work well, they do have some disadvantages. For example, known slide treatment devices include robotic components and other moving parts, increasing purchase costs and maintenance efforts. Further, known slide treatment devices do not have an operating mode that prevents boiling of the deparaffinization solution or other liquid being used and thus, permit solution to be wasted in the boiling process and/or possible damage to the specimen. In addition, known slide treatment devices do not monitor the level of the solution in the device and may permit the level of the solution drops below the slides, which can adversely affect the slide treatment process.

Thus, there is a need for a slide treatment device is cost-effective, easy to maintain, and that has improved capabilities that overcome the disadvantages of known slide treatment devices.

SUMMARY OF THE INVENTION

In one aspect, the slide treatment module of the present invention has two or more independently controllable processing tanks, so that different slide treatment processes can be run simultaneously. In another aspect, the slide treatment module of the present invention can also prevent boiling of a treatment solution, thereby substantially reducing the amount of solution used and hence, the cost of the slide treatment process. In yet another aspect, the slide treatment module of the present invention can also continuously monitor the level of the solution in each of the processing tanks and warn the user if the solution level drops to a level that may adversely effect the process. The slide treatment module of the present invention is especially useful as a pretreatment module in simultaneously performing deparaffinization and heat-induced epitope retrieval on formalin-fixed, paraffin-embedded tissue sections prior to immunostaining.

In accordance with the principles of the present invention and in accordance with the described embodiments, the present invention provides an apparatus for treating slides. In one embodiment, the apparatus has a base with a cavity and a heater located on or within a surface of the cavity. A tank, which supports a slide rack with the slides submerged in a slide treatment solution, is placed in the cavity with a tank surface immediately adjacent the heater. A temperature sensor is mounted in the base and is operable to provide a feedback signal representing a temperature of the liquid in the tank. A cover is removably hinged on the base to cover the tank. A control system is connected to the heater and the temperature sensor and has a user input/output that is operable to select a set temperature of the liquid and a cycle time.

In another embodiment of the invention, the apparatus has a plurality of cavities with a plurality of tanks mountable therein. Each cavity has a heater and temperature sensor, and the control system is connected to the heaters and temperature sensors and is operative to independently control a different slide treatment process in each of the tanks.

In a further embodiment of the invention, the tank has a liquid level sensor; and the control is operative to signal a user in response to detecting a low liquid level. In a still further embodiment, the control is effective to automatically lock the cover on the tank at the beginning of the slide treatment process and subsequently, automatically unlock the cover when the liquid has cooled to a finish temperature.

In additional embodiments of the invention, processes for treating slides include a preheat mode and/or a no-boil mode. The preheat mode initially brings the liquid up to a start temperature, and the no-boil mode maintains the temperature of the liquid just below its boiling temperature during the slide treatment process.

These and other objects and advantages of the present invention will become more readily apparent during the following detailed description taken in conjunction with the drawings herein.

DETAILED DESCRIPTION OF THE INVENTION

Figure 1:
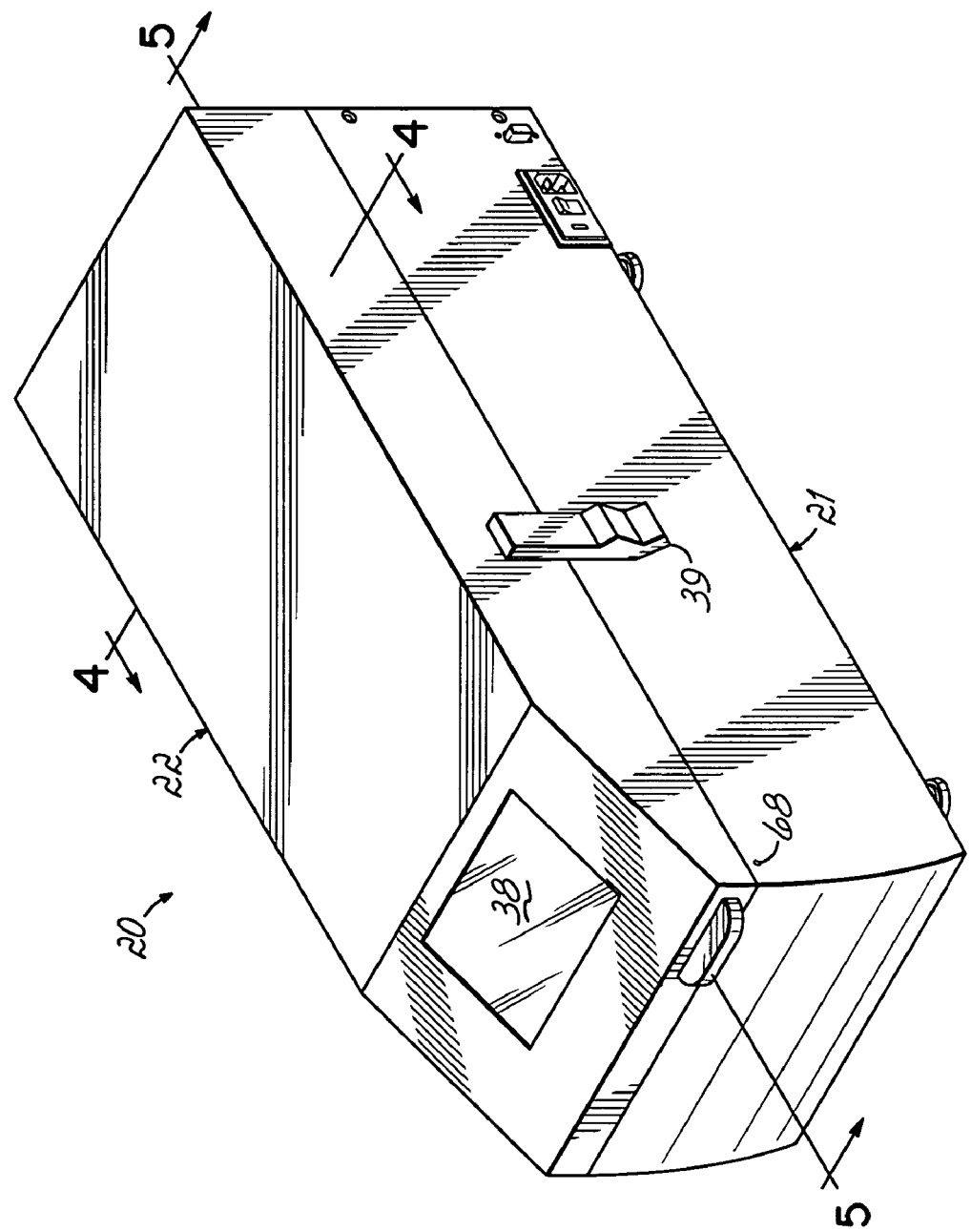
FIG. 1 is a perspective view of one embodiment of a slide treatment module with the cover closed in accordance with the principles of the present invention.
Figure 2:
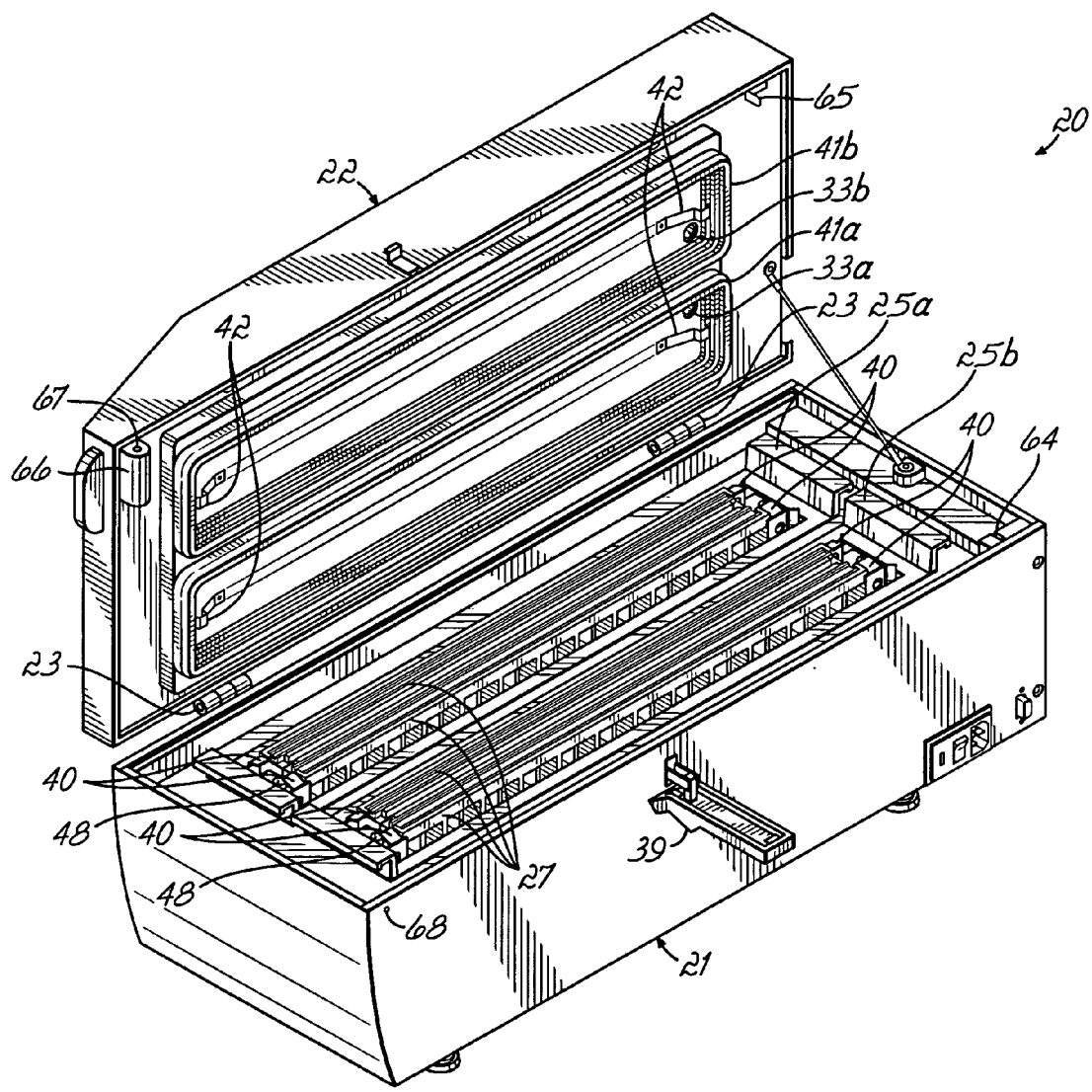
FIG. 2 is a perspective view of the slide treatment module of FIG. 1 with the cover open and the tanks and slide racks loaded in the slide treatment module.
Figure 3:
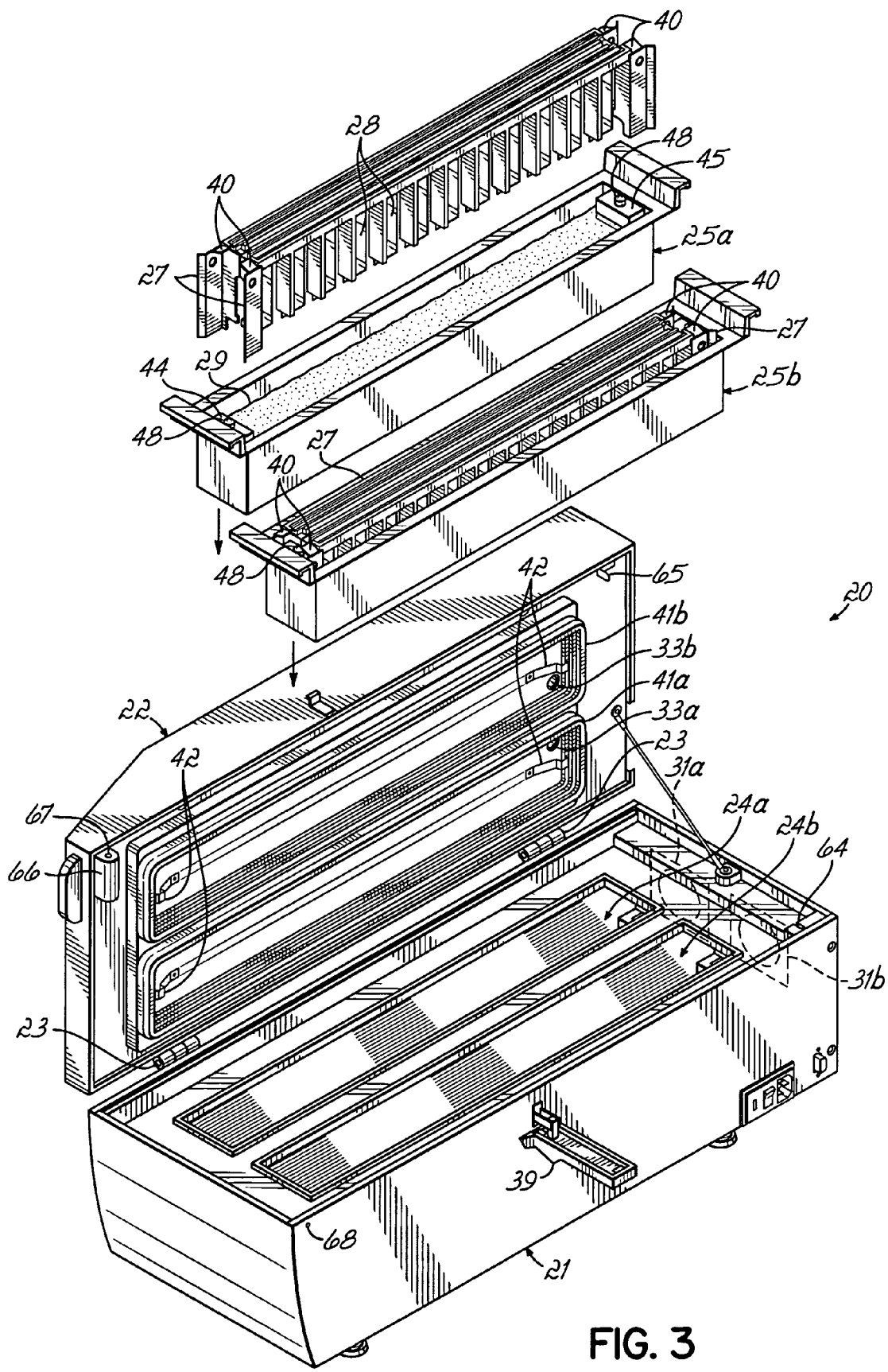
FIG. 3 is a perspective view of the slide treatment module of FIG. 1 with the cover open and showing the tanks and slide racks disassembled from the slide treatment module.

Referring to the embodiment shown in FIGS. 1, 2 and 3, a slide treatment module 20 has a base 21 and a removable cover 22 that is attachable to the base by hinges 23. The base 21 contains two cavities 24a, 24b that are sized to receive and support respective tanks 25a, 25b. Alternatively, the base 21 can contain more than two cavities 24. The tanks 25 are filled with a slide treatment solution or liquid 29, and slide racks 27 holding slides 28 are immersed in the solution. The cover 22 has seals 41a, 41b that surround the respective tanks 25a, 25b when the cover 22 is closed and locked with a manual latch 39.

Figure 4:
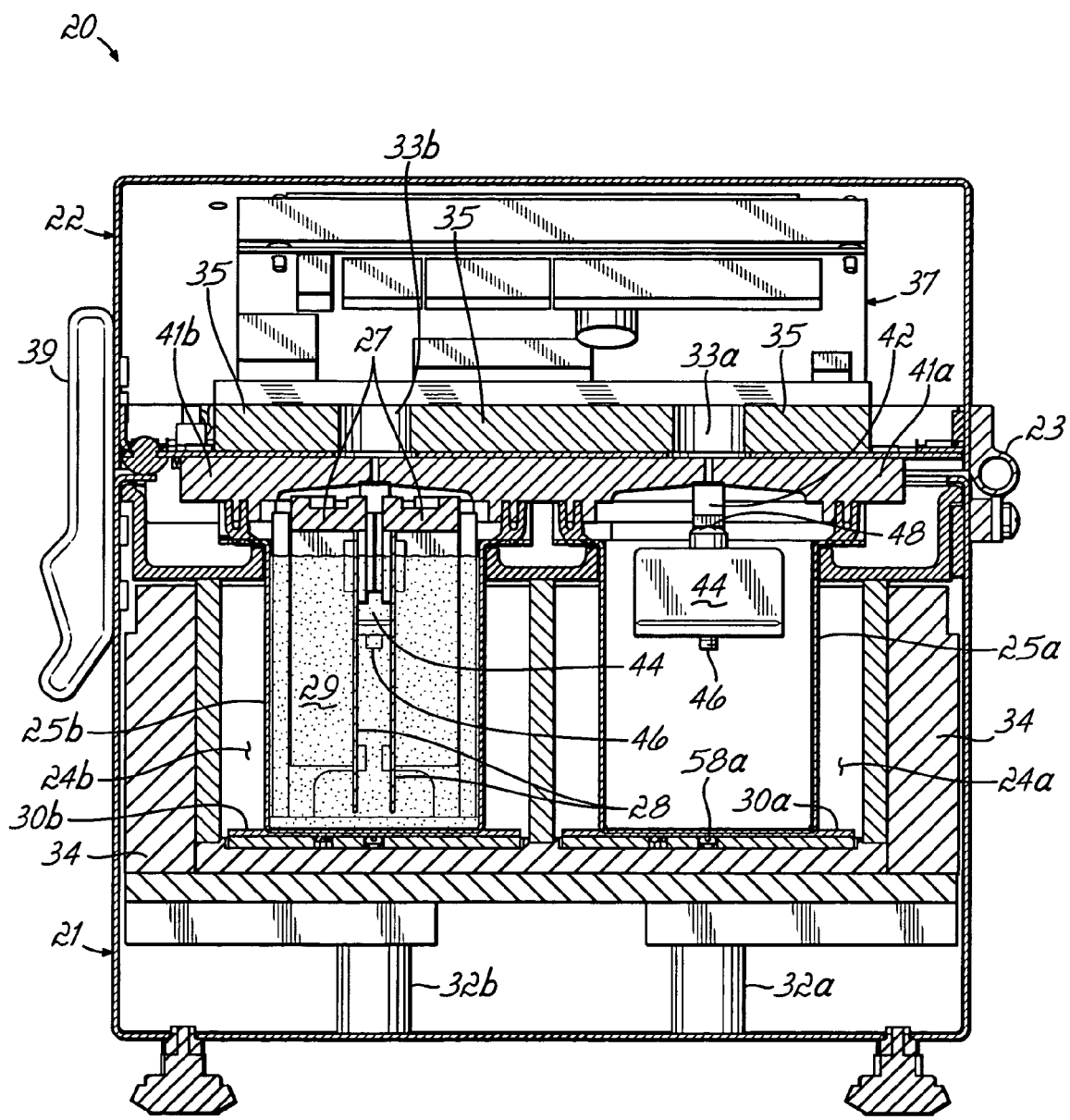
FIG. 4 is a cross-sectional view of the slide treatment module taken along the line 4-4 in FIG. 1.
Figure 5:
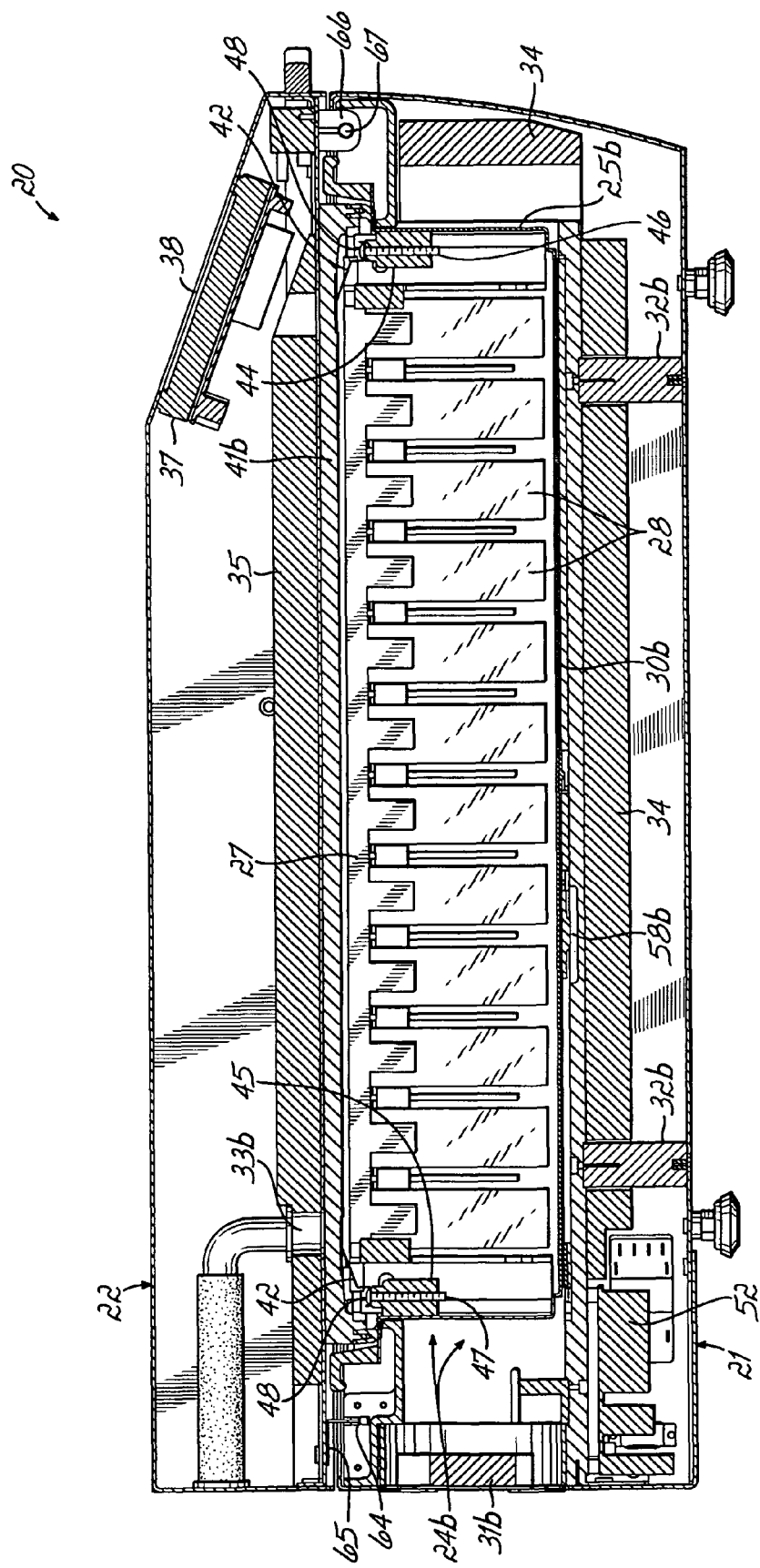
FIG. 5 is a longitudinal cross-sectional view of the slide treatment module taken along the line 5-5 in FIG. 1 and showing a cover position sensor.

Referring to an embodiment of FIGS. 3, 4 and 5, each of the tanks 25a, 25b has support blocks 44, 45 mounted at the tank end walls. Each pair of support blocks 44, 45 receives supports tabs 40 of slide racks 27 that hold slides 28 being treated in a solution 29 in a respective tank 25a, 25b. Each of the tanks 25a, 25b is designed to support two or more slide racks, for example, the slide racks that are used with any autostainer made by Lab Vision Corporation (Fremont, Calif.). Thus, after treatment, the slide racks 27 can be transferred directly to the autostainer without further handling. Each of the cavities 24a, 24b has a respective heater 30a, 30b on or within one or more surfaces of the cavities 24a, 24b, for example, the bottom surface of the respective cavities 24a, 24b. Cooling fans 31a, 31b are mounted in the end walls of respective cavities 24a, 24b. Each of the cavities 24a, 24b has respective drain lines 32a, 32b and respective vents 33a, 33b. Base insulation 34 surrounds the cavities 24a, 24b on three sides, and cover insulation 35 is provided over the cavities 24 when the cover 22 is closed. Each of the support blocks 44, 45 has a respective liquid level sensing screw 46, 47 mounted therein and extending downward into the a respective tank 25a, 25b.

Figure 6:
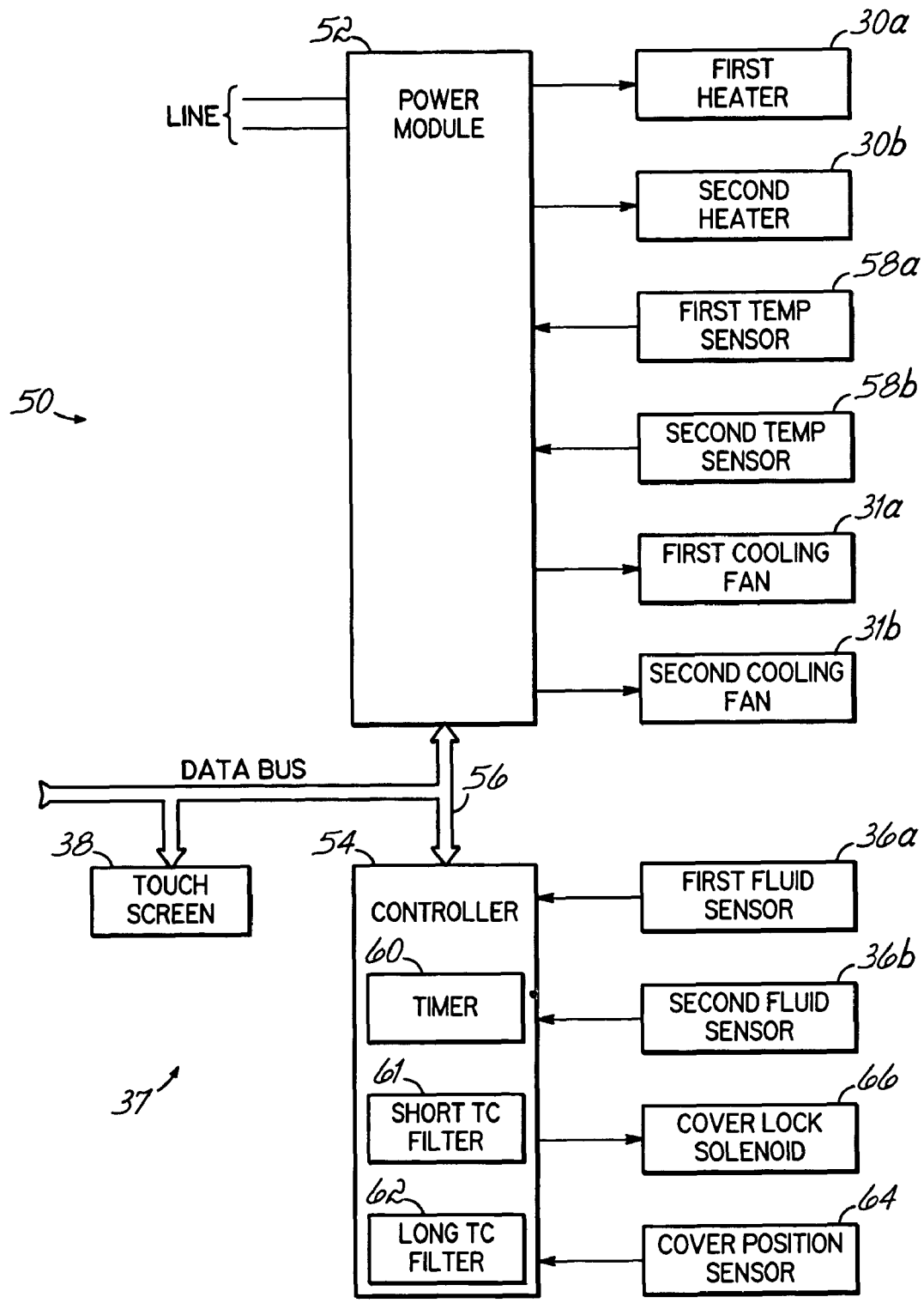
FIG. 6 is a schematic block diagram of a control system for operating the slide treatment module of FIG. 1.

In the embodiment shown in FIGS. 4, 5 and 6, a system control 50 includes a power module 52 mounted in the base 21 and a control module 37 mounted in the cover 22, which contains a controller 54 and touch screen 38 that provides a user input/output device. The touch screen 38 and controller 54 function together to provide a series of screens to a user. The screens permit the user to enter and store in the controller 54 set solution temperatures for each of the tanks 25a, 25b and cycle times for slide treatment processes for each of the tanks 25a, 25b. In another embodiment, screens allow the user to enter and store in the controller 54 whether a preheat cycle and/or a no-boil mode are enabled or disabled for each of the tanks 25a, 25b. The power module 52, programmable controller 54 and touch screen 38 are operatively connected together by means of a databus 56.

The controller 54 is also operative to detect a level of the solution in the tanks by detecting continuity between a pair of sensing screws 46, 46 located at opposite ends of each of the tanks 25a, 25b. If the solution boils away and drops below the level of the bottoms of the screws 46, 47 continuity is lost; and the controller 54 provides an error display on the touch screen 38 and/or an audible alarm. Further, if the controller 54 determines that the fluid is low when the cover is closed, an error display is generated; and the slide treatment cycle is disabled from running. The cavities 25a, 25b further have respective temperature sensors 58a, 58b that permit the controller 54 to detect a temperature of a solution in the respective cavities. The controller 54 further is able to detect when the cover is open and shut by monitoring the state of a cover position sensor 64 shown in FIGS. 5 and 6. For example, as the cover is closed, a tab 65 (FIG. 3) on the cover 22 actuates the cover position sensor 64, for example, a limit switch, located in the base 21. In addition, if the controller 54 determines the cover is closed, it is further operative to activate a cover lock solenoid 66 (FIGS. 3 and 6) on the cover 22, which drives a pin 67 through a hole 68 in the base 21, thereby preventing the cover 22 from being opened by the user.

In use, a user first inserts the tank 25b into the cavity 24b, and the tank 25b is located on or immediately adjacent to the heater 30b. The user then fills the tank 25b with a desired buffer or slide treatment solution, making sure that the solution level is above the bottoms of the liquid level sensing screws 46, 47. Next one or more slide racks 27 holding the slides 28 are placed in the solution-filled tank 25b submerging the slides in the solution. In an alternative process, prior to being placed in the tank 25b, the tank can be filled with the desired slide treatment solution and the slides placed therein. The cover 22 is then closed and locked with the manual latch 39. As the cover 22 is closed, spring contacts 42 bear against the heads 48 of the level sensing screws 46, 47 thereby providing electrical continuity from the screws 46, 47 to the controller 54.

The user then utilizes the touch screen 38 to input set temperatures and cycle times for the slide treatment process in each of the tanks 25a, 25b and optionally, enable a preheat mode and/or a no-boil mode for each of the tanks 25a, 25b. For any given slide treatment cycle, the operation of the tanks 25a, 25b is substantially identical; and therefore, only the slide treatment cycle for tank 25b will be described.

Figure 7:
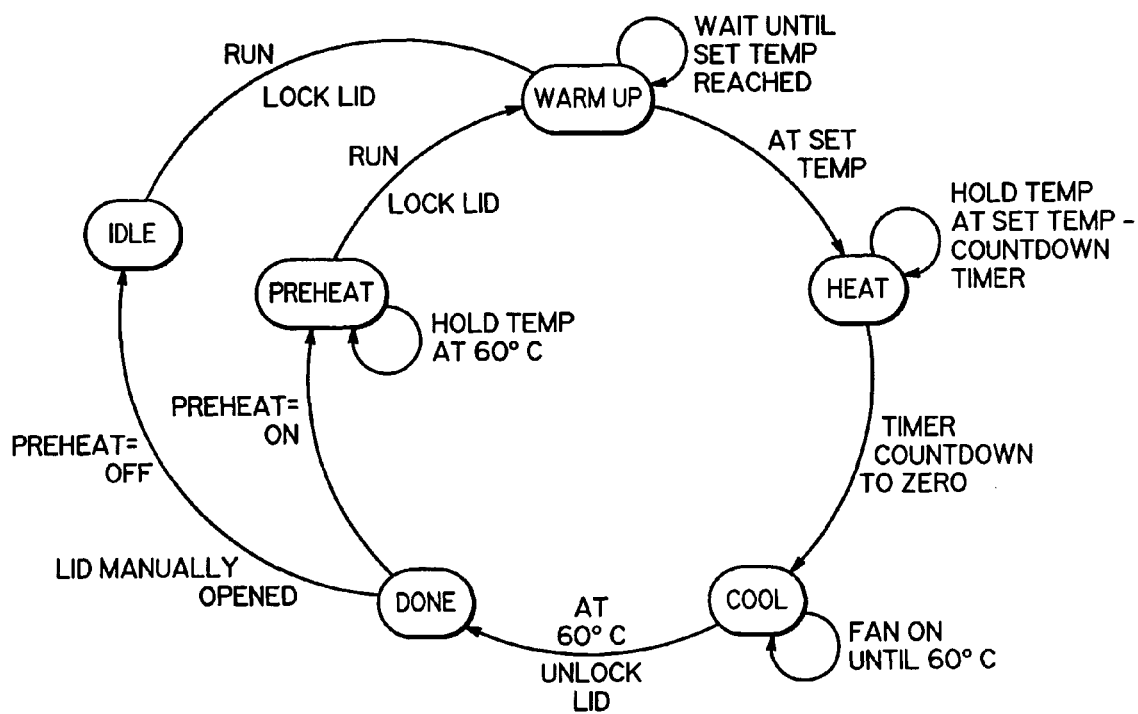
FIG. 7 is a schematic flow diagram of cycles of operation of the slide treatment module of FIG. 1.

Referring to the exemplary embodiment of FIG. 7, if a preheat mode is disabled, upon receiving a run command from the user via the touch screen 38, the controller 54 first monitors the state of the cover sensor 64. If the cover 22 is not closed, the controller 54 halts the cycle and creates an error display on the touch screen 38. If the cover 22 is closed, the controller 54 then activates the cover lock solenoid 66, which locks the cover 22 on the base 21, thereby preventing the user from opening the cover during the slide treatment cycle. Next, the controller 54 provides commands via the bus 56 to the power module 52 to turn on heater 30b. Simultaneously, the power module 52 monitors the temperature sensor 58b and provides a feedback signal to the controller 54 representing a temperature of the solution in tank 25b. The controller 54 initiates a warm-up mode by commanding the power module 52 to operate the heater 30b in a known manner, for example, using a PID loop, until the temperature sensor 58b detects a solution temperature substantially equal to the set temperature input by the user. At that point, the controller 54 starts an internal timer 60 that begins to time the slide treatment cycle; and the controller 54 continues to command the operation of the heater 30b to maintain the solution at the set temperature. Upon the controller 54 determining via the timer 60 that the duration of the slide treatment cycle is substantially equal to the cycle time input by the user, the controller 54 commands the power module 52 to turn off the heater 30b and turn on the cooling fan 31b. The controller 54 continues to monitor the first temperature sensor 58b until it detects a solution temperature substantially equal to a finish temperature, for example, 60° C., which is preset in the controller 54. At that point, the controller 54 deactivates the cover lock solenoid 66, which permits the user to utilize the manual latch 39 to open the cover 22.

If the user has enabled the preheat mode, upon receiving a run command from the user, the controller 54 commands the power module 52 to turn on the heater 30b until the controller detects that the temperature of the solution in the tank 25b is substantially equal to a start temperature, for example, 60° C. Thereafter, the controller 54 proceeds to actuate the cover lock solenoid 66, and the slide treatment cycle proceeds as previously described.

In the embodiment shown in FIG. 7, during a setup procedure, the user can use the touch screen 38 to select a no-boil feature that is operative during the warm-up cycle. Upon selecting the no-boil mode, the user also inputs, as a setpoint temperature, a temperature known to be above the boiling point of the solution or a maximum programmable setpoint temperature, for example, 112° C. In operation, during the warm-up mode, controller 54 monitors the temperature sensor 58. Upon detecting a solution temperature of about 90° C., the controller 54 executes the no-boil feature by monitoring the rate of temperature rise (dT/dt). The rate of temperature rise is detected by smoothing the temperature sensor readings or samples with a pair of averaging filters, a first filter 61 (FIG. 6) having a shorter time constant (tau 1) and a second filter 62 having a longer time constant (tau 2). Given a constant power input, the difference between the outputs from the two filters is substantially constant when the fluid temperature is well below its boiling point; but as the boiling point is approached, the outputs from the two filters begin to converge. Upon reaching the boiling point, the temperature rise of the solution ceases; and the outputs of the two filters are substantially the same. Just prior to reaching this steady state, the difference in output between the filters decreases to a defined convergence threshold. A theoretical convergence threshold is related to the two filter time constants by the following formula:

$$(T_{thres}) < k*(dT/dt)*(tau\ 2 - tau\ 1);\ where\ 0 < k < 1$$

Thus, the system design requires default values be chosen for k, the time constants of the two filters, the convergence threshold temperature and a setpoint temperature reduction. The selection of an optimum set of default values will depend on the volume of the tank, the applied power and the thermal load presented by the solution and the slides; and, as will be appreciated, the variables are often determined experimentally. With an applied power of approximately 350 watts and tank fluid volume of 1.5 liters, the temperature rate of change dT/dt is determined to be about 0.04° C. per second. One value of the constant k, for example, k=0.31, is a result of a design compromise between an adequately high fluid temperature on the one hand, and less steam generation, shorter convergence time, and immunity to spurious sensor readings on the other. Other default values empirically deemed to satisfy the stated tradeoffs are: $T_{thres}$=0.5° C., tau 2=50 seconds, and tau 1=10 seconds. However, as will be appreciated, tau 1 can range from about 5 to 10 seconds; tau 2 can range from about 25 to 50 seconds; but other values of those variables can be used.

The controller 54 monitors the convergence threshold temperature to determine when the solution approaches its boiling point. In one embodiment, upon detecting a convergence threshold temperature of about $T_{thres}$=1.0° C., the controller 54 reduces the programmed setpoint temperature to a new, lower setpoint temperature that is maintained for the remainder of the cycle. The new, lower setpoint temperature is calculated by reducing the output temperature of the short time-constant filter by about 1.0° C. The new, lower setpoint temperature is not displayed on the touch screen 38. Thereafter, upon the controller 54 detecting a convergence threshold temperature of $T_{thres}$=0.5° C., the controller 54 provides a "BOIL" display on the touch screen 38. The controller 54 then operates the heater 30b to maintain the solution in the tank 25b at the new, lower setpoint temperature. The remainder of the treatment cycle occurs below the boiling temperature thus permitting the specimen to simmer in the treatment liquid.

As will be appreciated, the above-described system can be designed in many different ways. For example, during the setup procedure, upon the user selecting the no-boil mode, the controller 54 can automatically establish an initial setpoint temperature equal to the maximum programmable setpoint temperature, for example, 112° C., thereby simplifying the no-boil mode programming. Further, in some embodiments, the convergence threshold temperature can be set to any value greater than zero, thereby attempting to maintain a liquid temperature below the boiling temperature. In other embodiments, the convergence threshold temperature can be set to zero, thereby allowing the liquid to reach the boiling temperature. All such embodiments provide a system that, given an initially programmed setpoint temperature in excess of the boiling temperature, automatically heats the liquid to, or a little less than, the boiling temperature, and thereafter, maintains the liquid at a simmering temperature less than the boiling temperature. Simmering, as opposed to boiling, greatly reduces risks of tissue damage and/or loss and prevents the rapid evaporation of treatment solution, so less solution is required for treatment. The no-boil mode requires no knowledge of the boiling point by the user and thus, makes operation of the module 20 substantially simpler than known devices.

The controller 54 also permits the user to interrupt or pause a cycle of operation in the tank 25b of the slide treatment module 20. Upon the user providing a pause command via the touch screen 38, the controller 54 shuts off the heater 30b, stops the countdown timer 60, if running, and unlocks the cover 22. Thus, pause allows the user access to the slides during the operation of a processing cycle. If a pause command causes a heater to be turned off during the no-boil mode when the liquid temperature is above 90° C., the above-described operation of the no-boil algorithm is interrupted. Further, the length of the pause in operation will impact the moving average value of liquid temperature provided by the two filters. In order to allow the output from the two filters to settle out after a pause operation, the controller 54 requires that the liquid temperature be above 90° C. and the heater be turned on again for a minimum period of time before the outputs of the two filters are again monitored to detect a convergence threshold temperature. The minimum period of time should be adequate for the two filters to establish a valid trajectory after power is restored, for example, the minimum period of time can be substantially equal to the longer time constant tau 2.

Thus, the slide treatment module 20 provides a variety of automated slide treatment cycles that can be used to provide a wide range of slide treatment applications. The automated operation easily provides more consistent, repeatable processes with less trial and error, which allows a less skilled user to operate the module. With the two or more independently controllable tanks 25a. 25b, the slide treatment module 20 can run two or more different slide treatment processes simultaneously, thereby increasing the throughput of the module. Further, the no-boil mode prevents wasting solution from boiling, thereby reducing the amount of solution used and hence, reducing the cost of the slide treatment process. The slide treatment module 20 also continuously monitors the level of the solution in each of the processing tanks and warns the user if the solution level drops to a level that may adversely affect the process.

While the slide treatment module 20 can be used as a pretreatment module to simultaneously perform deparaffinization and heat-induced epitope retrieval on fixed, paraffin-embedded tissue sections prior to immunostaining, other uses employing heating in solution are anticipated.

While the invention has been illustrated by the description of several embodiments and while the embodiments have been described in considerable detail, there is no intention to restrict nor in any way limit the scope of the appended claims to such detail. Additional advantages and modifications will readily appear to those who are skilled in the art. For example, in the described exemplary embodiments, in the no-boil mode, a new, lower setpoint temperature is determined from the output temperature of the lower time constant filter. In an alternative embodiment, the new, lower setpoint temperature can be determined by reducing a reading of the temperature sensor by a fixed temperature increment in response to a predetermined value of the convergence threshold. In a further alternative embodiment, during a setup procedure, the controller 54 provides a user with a selection of temperature reductions, for example, 0.5, 1.0, 1.5 and/or 2.0° C. or more; and the user-selected temperature reduction is used to calculate a new, lower setpoint temperature.

In the described embodiments, the user operates a touch screen 38 to input a single setpoint temperature and a single cycle time for each of the tanks 25a, 25b. However, in other applications and embodiments of the slide treatment module 20, the controller 54 can be programmed to execute slide treatment processes that utilize multiple setpoint temperatures over multiple time periods. Further, those multiple setpoint temperatures and time periods can be user selectable using the touch screen 38. In addition, the controller 54 has the capability of controlling the rate of temperature rise or drop during heating or cooling, respectively. The controller 54 has the further capability of capturing real time processing conditions for display on the touch screen 38 or for subsequent quality control analysis or other processing.

In the described embodiments, the data bus 56 provides communications between the power module 52, the controller 54 and touch screen 38. However, in alternative embodiments, the data bus 56 can be connected to a local area network, a wide area network or the internet, which would allow the operation of the slide treatment module 20 to be monitored from a remote location. Thus, real time processing conditions can be captured and stored remotely for quality control analysis and/or as part of a history of the material being processed. In addition, such a network connection also allows the slide treatment module 20 to be programmed from a remote location.

In the described embodiments, the controller 54 provides displays on the touch screen 38 in response to detecting error conditions such as a low solution level. In other embodiments, error conditions can be signaled to a user with lights, sounds or other sensory-perceptible alarms or indicators.

Further, in the described embodiments, the cover 22 prevents a user from being exposed to a boiling liquid, provides a slight pressure gradient to allow a slightly higher temperature and acts as an insulator to provide more precise temperature control. However, in alternative embodiments, in applications where less precise temperature control is acceptable, the cover 22 can be eliminated from the module 20.

In the described embodiments, a temperature sensor 58 is mounted on a bottom wall of cavity 24. In alternative embodiments, solution temperature can be detected directly, for example, by a temperature probe immersed in the solution, or indirectly, for example, by an infrared sensor or other remote temperature measuring device.

Therefore, the invention in its broadest aspects is not limited to the specific details shown and described. Consequently, departures may be made from the details described herein without departing from the spirit and scope of the claims that follow.

What is claimed is:

1. An apparatus for treating slides in a slide rack, the apparatus comprising:
   a base comprising a cavity disposed in the base;
   a heater disposed immediately adjacent a surface of the cavity;
   a tank removably supportable in the cavity with a tank surface immediately adjacent the heater, the tank adapted to receive a liquid and the slide rack with the slides disposed in the liquid;
   a temperature sensor mounted in the base and operable to provide a feedback signal representing a temperature of the liquid in the tank; and
   a control system electrically connected to the heater, the temperature sensor and comprising:
      user input/output operable to select an operating mode for heating the liquid,
      a longer time constant filter responsive to temperature samples of the liquid and producing a first average temperature value,
      a shorter time constant filter responsive to temperature samples of the liquid and producing a second average temperature value,
   the control determining a temperature of the liquid being about equal to the liquid's boiling temperature in response to a difference between the first average temperature value and the second average temperature value being substantially equal to a predetermined value.

2. The apparatus of claim 1 wherein the user input/output is operable to provide a setpoint temperature in excess of the liquid's boiling temperature.

3. The apparatus of claim 1 further comprising a liquid level sensor mounted in the tank for detecting a level of the liquid in the tank.

4. The apparatus of claim 1 wherein the heater comprises a resistance heater.

5. The apparatus of claim 1 wherein the heater comprises a resistance heater supported by silicone.

6. The apparatus of claim 1 wherein the control system comprises:
   a power module connected to the heater and the temperature sensor; and
   a programmable controller connected to a power module and the user input/output.

7. The apparatus of claim 6 wherein the control system further comprises a data link in electrical communications with the power module, the programmable controller and the user input/output.

8. The apparatus of claim 1 further comprising:
   a cover removably mountable on the base, the cover having an open position relative to the base and a closed position relative to the base in which the tank is covered; and
   a cover lock electrically connected with the control system, the cover lock configured to automatically lock the cover with the base in response to the control system sensing the closed position of the cover.

* * * * *